United States Patent [19]

Geus

[11] Patent Number: 4,870,670
[45] Date of Patent: Sep. 26, 1989

[54] X-RAY SCANNER WITH SECONDARY RADIATION DETECTOR

[75] Inventor: Georg Geus, Wiesbaden, Fed. Rep. of Germany

[73] Assignee: Heimann GmbH, Wiesbaden, Fed. Rep. of Germany

[21] Appl. No.: 253,484

[22] Filed: Oct. 5, 1988

[30] Foreign Application Priority Data

Oct. 19, 1987 [DE] Fed. Rep. of Germany ....... 3735347

[51] Int. Cl.⁴ .......................................... G01N 23/203
[52] U.S. Cl. ....................................... 378/87; 378/62; 378/90
[58] Field of Search ................................... 378/86–90, 378/6–7, 57, 62

[56] References Cited

U.S. PATENT DOCUMENTS

```
3,927,318  12/1975  Macovski .
4,047,029   9/1977  Allport .................................. 378/90
4,229,651  10/1980  Danos .
4,366,382  12/1982  Kotowski .
4,495,636   1/1985  Jacobs et al. .
```

FOREIGN PATENT DOCUMENTS

```
2845369  4/1980  Fed. Rep. of Germany .
2054319  2/1981  United Kingdom .
```

OTHER PUBLICATIONS

"On The Sensitivity and Application Possibilities of a Novel Compton Scatter Imaging System", Harding, IEEE Transactions on Nuclear Science, vol. NS-29, No. 3, Jun. 1982, pp. 1260–1265.
"Luggage Control With X-Ray Eyes," Linkenbach et al., Siemens Review, vol. 48, No. 6, Nov./Dec. 1981.

Primary Examiner—Janice A. Howell
Assistant Examiner—David P. Porta
Attorney, Agent, or Firm—Hill, Van Santen, Steadman & Simpson

[57] ABSTRACT

An article inspection system has separate detectors for primary radiation and scattered radiation which are generated by an article upon being irradiated with X-radiation. The scattered radiation detector is disposed so that no primary radiation is incident thereon. The primary radiation detector is scanned at a frequency to produce a primary radiation image. The scattered radiation incoming to the scattered radiation detector is modulated at a frequency synchronized with the scanning frequency for the primary radiation detector, so that only scattered radiation is incident on the scattered radiation detector which emanates from the region of the article which is currently being scanned for primary radiation.

7 Claims, 2 Drawing Sheets

X-RAY SCANNER WITH SECONDARY RADIATION DETECTOR

BACKGROUND OF THE INVENTION

1. Field of the Invention

The present invention relates to an article inspection system including separate detectors for primary and scattered radiation.

2. Description of the Prior Art

Article inspection systems are known in the art wherein the article, such as baggage, to be inspected is moved through a fan-shaped x-ray beam. A line of individual detectors are disposed at an opposite side of the article, so that radiation attenuated by the article is incident on the detectors. The article is moved through the x-ray beam at a defined speed, so that it is scanned strip-by-strip by the detector line. The detector line, which consists of a plurality of individual detector elements, is scanned so that the output signals of the detectors are serially obtained, and are interpreted either in real time, after conversion to digital values, or are written into a memory for constructing a video image.

It is also known that scattered rays arise during the irradiation of the articles. It is known that certain types of material such as, for example, plastics in general, and plastic explosive in particular, being less absorbent to x-radiation, generate relatively high amounts of scattered radiation.

SUMMARY OF THE INVENTION

It is an object of the present invention to provide an x-ray scanner which detects scattered radiation from an article being inspected, and constructs a scattered ray image therefrom.

The above object is achieved in accordance with the principles of the present invention in an article inspection system wherein a modulator is provided which modulates the incoming scattered radiation incident on the scattered ray detector. The detector for the primary radiation is scanned at a scanning frequency, and the modulator for the scattered ray detector is synchronized to this scanning frequency so that it passes scattered rays to the scattered ray detector emitted only by that region of the article which is currently being scanned for primary radiation. The scattered ray detector system thus acquires signals from only the scattered rays emitted by regions which contribute to the visual portrayal of the primary radiation image. By synchronizing the modulator with the scanning frequency of the primary radiation detector line, only that portion of the scattered rays is acquired which arises in the region of the article for which a primary radiation signal is currently being detected.

To correctly reproduce the respective detector signals, it is necessary to provide spatially separate reception regions for the primary radiation and the scattered radiation. The radiation proceeding perpendicular to the direction of movement of the articles is already collimated upon exiting the x-ray source, and thus a determination of the scan intervals to correspondingly operate the scattered radiation modulator is necessary only for a plane disposed perpendicularly relative to the conveying direction. To this end, a rotating modulator is arranged in front of the scattered ray detector. The rotating modulator is in the form of a drum having a plurality of slots therein which respectively define reception sectors which pass through the scan region due to the rotary motion of the drum.

DESCRIPTION OF THE PREFERRED EMBODIMENTS

Figure 1:
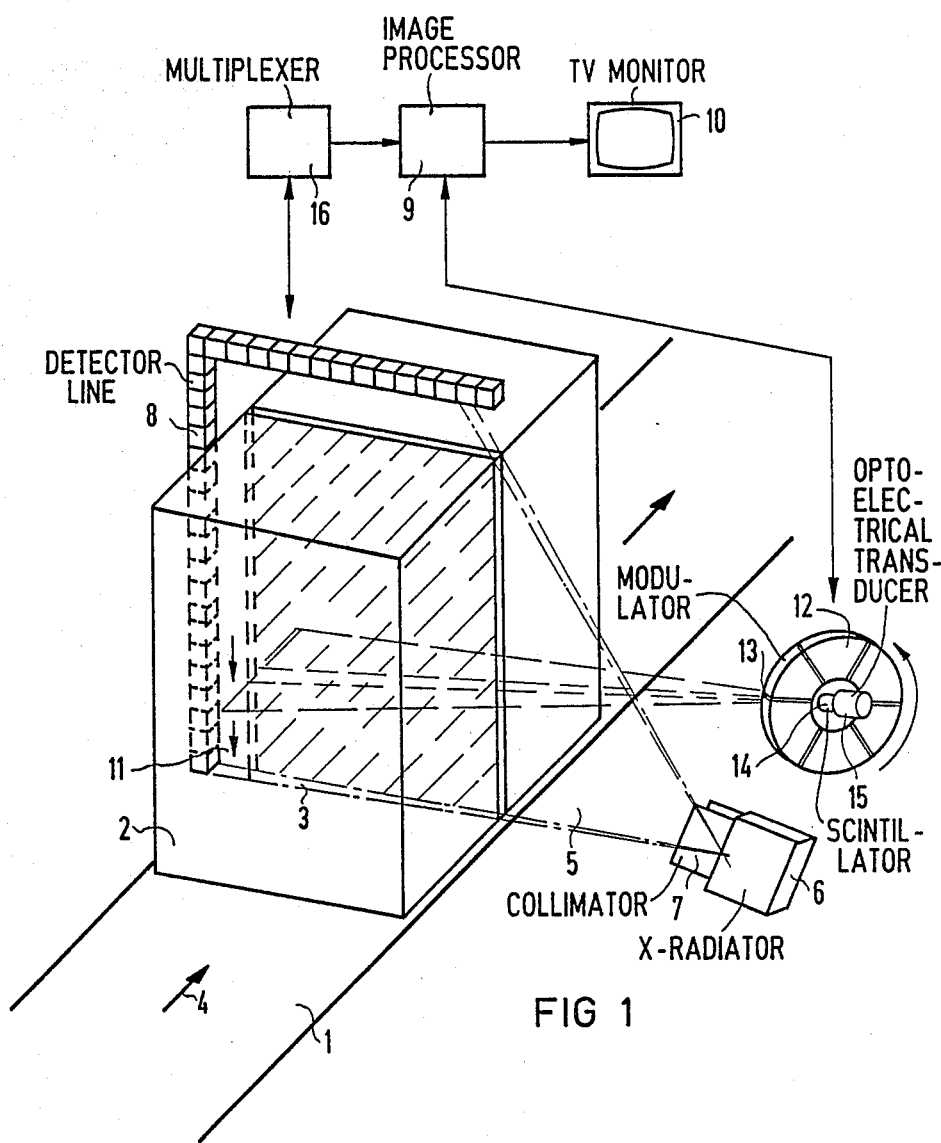
FIG. 1 is a perspective view of an x-ray scanner constructed in accordance with the principles of the present invention, showing electronic components in schematic block diagram format.

As shown in FIG. 1, an x-ray scanner constructed in accordance with the principles of the present invention includes a conveyor belt 1 on which an article 2 being inspected is moved in the direction of the arrow 4 through a fan-shaped x-ray beam 5. The x-ray beam 5 is generated by an x-radiator 6, and is gated by a collimator 7. A transverse slice 3 of the article 2 is irradiated, and the primary attenuated radiation is incident on an angled detector line 8, consisting of a number of individual detectors. The detector line 8 is scanned at a scanning frequency by a multiplexer 16, so that the respective signals from the individual detectors are serially obtained, and those signals are converted into signals from which a visible image can be constructed by an image processor 9. These signals correspond to the x-ray shadow image of the region of the article 2 which was irradiated by the x-ray beam 5. The image is visually displayed on a TV monitor 10.

The article 2 also emits scattered radiation as a result of being irradiated by the x-ray beam 5. A scattered radiation detector system is provided to document this radiation. The scattered radiation detector system includes a scintillator 14, an opto-electrical transducer 15 and a modulator 12. The scattered radiation detector system is disposed outside of the examination space 11, so that primary radiation is not incident thereon. The modulator 12 is in the form of a drum having a central opening in which the scintillator 14 and the optoelectrical transducer 15 are disposed.

The modulator 12 has a plurality of slotted diaphragms 13 extending radially from the central opening. The drum 12 is rotated, as indicated by the arrow, so that the diaphragms 13 define a plurality of scattered radiation scanning sectors which move through the slice defined by the collimator 7 at a speed corresponding to the rotational speed of the drum. This rotational speed of the modulator 12 is synchronized to be the same as the scanning frequency of the detector line 8. Thus the scattered radiation incident on the scattered radiation detector, i.e., the scintillator 14, will be emitted only by that region of the article 2 which is currently being scanned for primary radiation. A scattered radiation image precisely corresponding to the shadow image, constructed from the primary radiation, can thus be simultaneously and separately constructed.

The secondary radiation image can be separately displayed, or the output signals from the transducer 15 can be serially supplied to the image processor 9, as shown in FIG. 1, so that the scattered ray distribution can be shown, emphasized if needed, on the monitor 10. On a color monitor, the scattered ray information may be chromatically underlayed beneath the shadow image. The color saturation is a measure of the intensity of the scattered rays.

Figure 2:
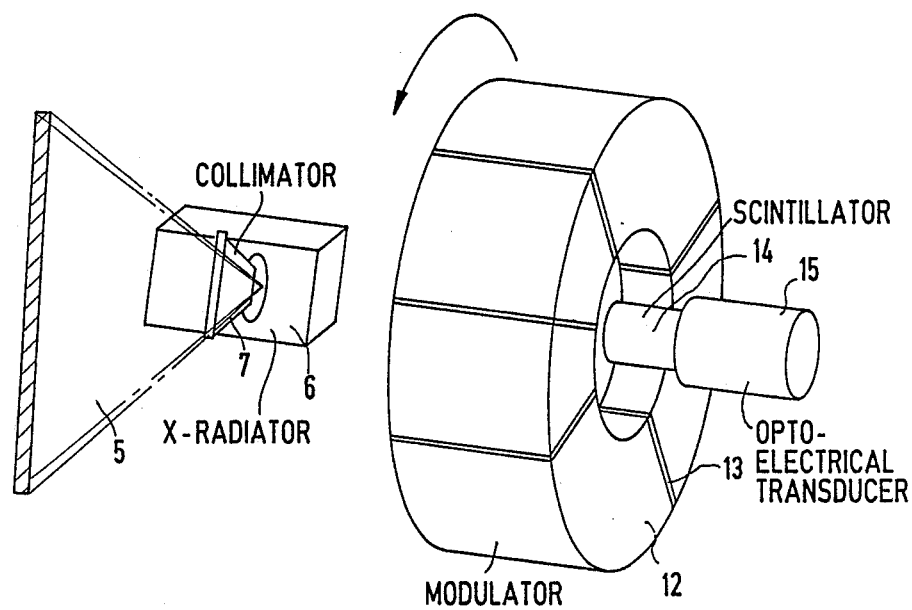
FIG. 2 is an enlarged view showing the relationship of the x-ray source and the scattered radiation detector.

The scattered ray detector system is shown in enlarged detail in FIG. 2. The reception angle for the incoming scattered radiation is determined by the width of the slots 13. In the embodiment shown in FIG. 2, serial scanning of the region of the article 2 ensues six times during one revolution of the drum.

The scintillator 14 in the embodiment of FIG. 2 is a rod-shaped detector, having a length roughly corresponding to the width of the drum, and disposed in the central opening of the modulator 12. It is preferable to arrange the reception system so that the scintillator 14 is disposed perpendicularly to the primary radiation beam 5, preferably along a line passing through the focal spot from which the primary radiation beam 5 emanates. This arrangement results in minimum geometrical distortions. The scintillator 14 may consist of light-sensitive conductors with following photomultipliers. It is also possible to use x-ray sensitive semiconductors or Geiger counter tubes as the scattered ray detector.

The protrayal of the primary radiation image and the scattered radiation image can be undertaken simultaneously or in chronological succession in monochromatic or polychromatic format on one or more monitors. Best results are obtained, however, in the embodiment of a chromatically underlayed simultaneous reproduction on one monitor, as shown in FIG. 1.

The modulator 12 having slotted diaphragms 13 constitutes a collimator wheel whose rotation is synchronized with the scanning frequency of the detector line 8 which is determined by the multiplexer 6. Accordingly, the modulator 12 admits only those scattered rays to the scintillator 14 which arise in the region of the article 2 for which primary radiation is also being currently detected.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray scanner for inspecting an article comprising:
   means for generating a fan-shaped x-ray beam;
   means for moving said article through said x-ray beam so that said article is irradiated thereby and generates primary radiation and scattered radiation;
   a primary radiation detector line consisting of a plurality of detector elements, each detector element receiving primary radiation from a region of said article and generating a signal corresponding thereto;
   means for scanning said elements of said primary radiation detector line at a scanning frequency for generating a primary radiation image of said article;
   means for detecting said scattered radiation disposed so that said primary radiation is not incident thereon; and
   means for modulating said scattered radiation incident on said means for detecting scattered radiation at a frequency synchronized with said scanning frequency so that only scattered radiation is incident on said means for detecting scattered radiation which is emitted by a region of said article currently being scanned for primary radiation.

2. An x-ray scanner as claimed in claim 1, wherein said means for modulating has a plurality of slotted diaphragms which collimate said scattered rays.

3. An x-ray scanner as claimed in claim 2, wherein said means for modulating is a rotating drum having a central opening in which said means for detecting said scattered radiation is disposed, and wherein said slotted diaphragms extend radially from said central opening.

4. An x-ray scanner as claimed in claim 1, further comprising mean for simultaneously visually protraying said primary radiation image and data corresponding to said scattered radiation from said means for detecting said scattered radiation.

5. An x-ray scanner for inspecting an article comprising:
   means for generating a fan-shaped x-ray beam;
   means for moving said article through said x-ray beam so that said article is irradiated thereby and generates primary radiation and scattered radiation;
   a primary radiation detector line consisting of a plurality of detector elements, each detector element receiving primary radiation from a region of said article and generating a signal corresponding thereto;
   means for scannng said elements of said primary radiation detector line at a scanning frequency;
   image processing means for generating a primary radiation image of said article from said signals of said elements of said primary radiation detector line;
   means for visually displaying said primary radiation image;
   means for detecting said scattered radiation disposed so that primary radiation is not incident thereon; and
   a rotatable drum having a central opening receiving said means for detecting said scattered radiation and a plurality of slotted diaphragms extending radially from said central opening, said drum rotating at a speed synchronized with said scanning frequency so that said slotted diaphragms define a sector of scattered radiation which moves through said article so that only scattered radiation is incident on said means for detecting which is emitted by a region of said article currently being scanned for primary radiation.

6. An x-ray scanner as claimed in claim 5, wherein said means for detecting said scattered radiation is connected to said image processor means for combining data corresponding to said scattered radiation with said primary radiation image for simultaneous display therewith on said means for displaying.

7. A method for operating an x-ray scanner for inspecting an article comprising the steps of:
   generating a fan-shaped x-ray beam;
   moving an article to be inspected through said x-ray beam and irradiating said article with x-ray so that said article generates primary radiation and scattered radiation;
   detecting said primary radiation generated by said article in a primary radiation detector line including a plurality of detector elements, each detector element receiving said primary radiation from a region of said article and generating a signal corresponding thereto;
   scanning the elements of said primary radiation detector line at a scanning frequency and generating a primary radiation image of said article from the signals of said elements;

detecting said scattered radiation generated by said article isolated from said primary radiation; and modulating the scattered radiation prior to detecting said scattered radiation, at a frequency synchronized with said scanning frequency so that only scattered radiation is detected which corresponds to a region of said article currently being scanned for primary radiation.

* * * * *